United States Patent [19]

Bode

[11] Patent Number: 5,195,947
[45] Date of Patent: Mar. 23, 1993

[54] CALIBRATED CERVICAL TRACTION DEVICE

[76] Inventor: Gerd B. Bode, 3601 E. Cherry Street, Seattle, Wash. 98122

[21] Appl. No.: 776,846

[22] Filed: Oct. 15, 1991

[51] Int. Cl.⁵ .............................................. A61F 5/08
[52] U.S. Cl. ...................................... 602/18; 602/17; 602/32
[58] Field of Search ...................... 128/75, 76 R, 87 B, 128/DIG. 23, 84 C; 602/17, 18, 32, 36

[56] References Cited

U.S. PATENT DOCUMENTS

| | | |
|---|---|---|
| 2,736,314 | 2/1956 | Hale . |
| 3,776,224 | 12/1973 | McFarland . |
| 3,957,040 | 5/1976 | Calabrese . |
| 4,541,421 | 9/1985 | Iversen et al. . |
| 4,620,530 | 11/1986 | Lanier et al. . |
| 4,735,196 | 4/1988 | Krag et al. . |
| 4,890,605 | 1/1990 | Rosendale . |
| 4,955,368 | 9/1990 | Heimann . |
| 5,046,490 | 9/1991 | Young et al. . |

OTHER PUBLICATIONS

"PMT Presents The NEW MRI Compatible Halo System," Progress Mankind Technology flyer.
"Application Instructions for Carbon One Cervical/-Thoracic Orthosis," Levtech instruction pamphlet, which makes note of U.S. Pat. No. 4,735,196.
"JMS Halo Traction System II," Jerome Medical Systems, Inc. flyer.
"Ace Cervical Traction Equipment, Including the New Trippi-Wells Tongs and Mark III Halo," ACE booklet.

Primary Examiner—Richard J. Apley
Assistant Examiner—Linda C. M. Dvorak
Attorney, Agent, or Firm—Seed and Berry

[57] ABSTRACT

A cervical traction device includes a vest to be worn by a patient with a spine or neck injury, a halo adapted to be secured to the patient's head, support rods interconnecting the halo and the vest, and an expansion member disposed between the halo and the support rods for adjusting the supporting force applied to the halo. The expansion member includes a calibrated scale for measuring and displaying the supporting force so that a balanced supporting force can be applied to the halo.

16 Claims, 4 Drawing Sheets

CALIBRATED CERVICAL TRACTION DEVICE

TECHNICAL FIELD

This invention relates to traction devices, and more particularly, to cervical traction devices for supporting the head during treatment of a neck or spinal injury.

BACKGROUND OF THE INVENTION

Cervical traction equipment has long been used to support the head during treatment and rehabilitation of a neck or spinal injury. In cases where the injury permits patient mobility, it is often desirable to support the head by means of a ring or "halo" which is rigidly affixed to the skull of the patient. The halo is typically supported by means of rods or other connecting members connected to a vest-like apparatus worn on the torso of the patient. There are usually two or four such connecting members, generally spaced symmetrically on either side of the patient's head and attached to the chest and back panels of the vest. In the final adjustment of such equipment, the connecting members are clamped or bolted in the desired positions on the halo so as to exert an upward supporting force on the halo and skull. The counterforce is supplied by the vest, which fits over the shoulders of the patient or, in other cases, may rest on the pelvis.

Making the final adjustments of traditional cervical traction equipment is generally a subjective procedure. The connecting members are bolted to the halo to provide the desired supporting forces based on the collective opinions of the clinician and the patient. The clinician typically will place the patient in a prone position and then pull on the patient's head or straighten the patient's neck while tightening the bolts or other fastening device while inquiring of the patient as to any changes in sensation that are experienced. The subjective responses from the patient are usually major determinants in the final adjustment of the connecting members and bolts and their applied forces.

A major problem with respect to traditional techniques of adjusting known cervical traction equipment is that they lack precision because they depend on the sensations of a patient who is unaccustomed to such equipment. An additional problem with respect to such methods is that cervical injuries are often accompanied by some degree of nerve damage, causing numbness or paralysis; hence, the ability of the patient to report sensatory changes may be limited. Furthermore, the traditional subjective approach to adjusting the supporting force applied to the halo is deficient even in the basic ability to precisely apply balanced supporting forces around the halo and skull since the supporting force of the connecting member can vary from each other.

SUMMARY OF THE INVENTION

A primary object of the invention, therefore, is to provide a cervical traction apparatus capable of being adjusted on an objective basis.

Another object of the invention is to provide a cervical traction apparatus that can be quantitatively adjusted so that a supporting force of a specific magnitude can be applied to the halo to support the patient's head.

Still another object of the invention is to provide a cervical traction device that includes a means for measuring and displaying the magnitude of the supporting force being applied to the halo.

Yet another object of the invention is to provide a cervical traction device that includes individual adjustable support members so that a balanced supporting force to the head can be applied to the patient's head.

Another object of the invention is to provide a cervical traction device wherein the supporting force can be adjusted after a halo has been secured to the patient's head and after the support rods have been coupled between a vest worn by the patient and the halo.

The foregoing objects, as well as other objects that will become apparent from the disclosure below, are achieved by a cervical traction device comprising a vest to be worn by a patient with a spine or neck injury, a halo adapted to be secured to the patient's head, support rods interconnecting the halo and the vest, and an expansion member disposed between the halo and the supports rods for adjusting the supporting force applied to the halo. The expansion member includes a calibrated scale for measuring and displaying the supporting force so that a balanced supporting force can be applied to the halo.

DETAILED DESCRIPTION OF THE INVENTION

Figure 1:
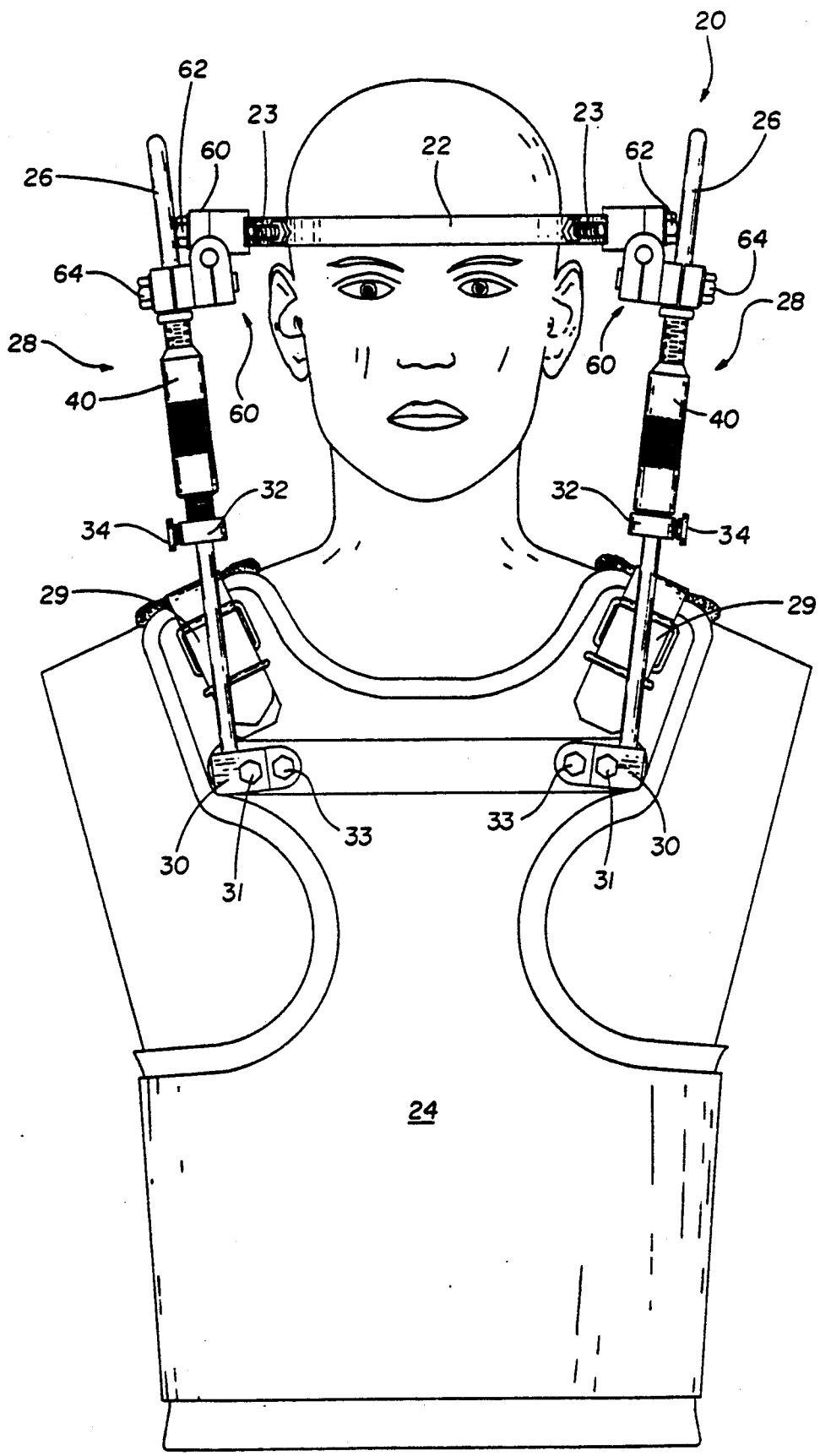
FIG. 1 is a front elevational view of the cervical traction device of the present invention as worn by a patient.

With reference to FIG. 1, the present invention generally involves a cervical traction device 20 to be worn by a patient with a spinal or neck injury. One embodiment of the traction device 20 comprises a vest 24 adapted to be worn about the torso of the patient, a halo 22 adapted to be secured to the head of the patient, multiple support rods 26, each being secured at one end to the halo 22 and at an opposite end to the vest 24 to provide an upward, supporting force upon the halo 22, and an expansion member 28 for adjusting the upward force applied to the halo 22. This type of cervical traction device is intended to be worn by the patient to immobilize the neck and spine so that, for example, a cervical spine fracture can properly heal.

Figure 2:
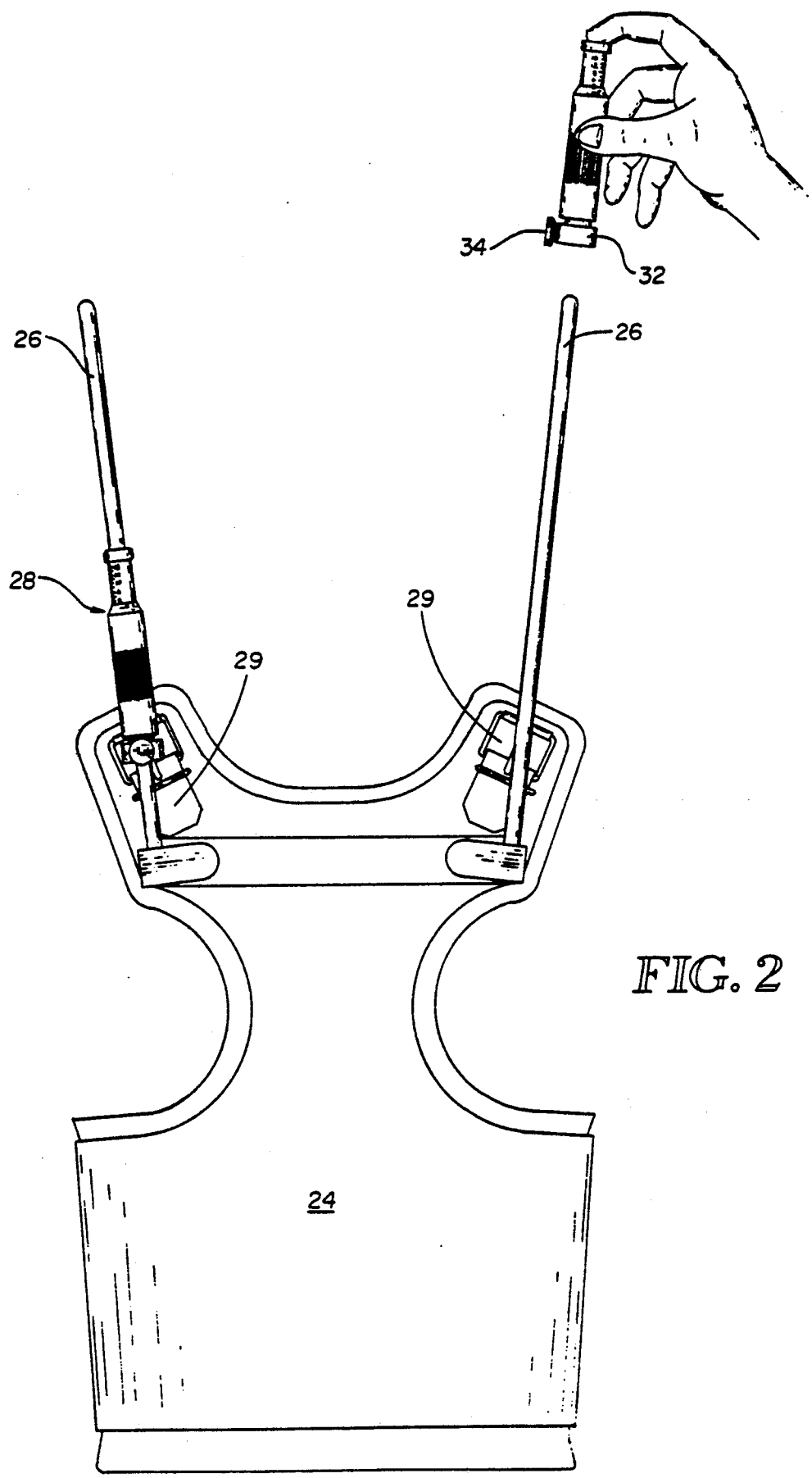
FIG. 2 is a front elevational view of the vest, support rods, and adjustment means of the present invention.

Referring now to FIG. 1, the vest 24 is made to fit easily and comfortably around the torso of the patient. Preferably, the vest is designed to take the load of the support rods 26 circumferentially about the patient's torso rather than at the patient's shoulders. Although the embodiment of FIGS. 1 and 2 shows a torso vest 24 for supporting the load of the support rods 26, the present invention is suitable for any type of body support structure to be worn by the patient, such as, for example, a pelvic girdle.

The vest 24 comprises a chest panel and a back panel (not shown). The two panels are joined by multiple belt/buckle assemblies 29 which are adjustable to suit the patient's upper body. Although not shown in FIGS. 1 and 2, multiple belt/buckle assemblies may be used at the sides of the chest and back panels of the vest 24 to allow for further adjustments.

The support rods 26 are coupled to the vest 24 by means of connecting members 30. An end of each support rod 26 is inserted into the member 30, and a bolt 31 is tightened to secure the rod 26 in place. The connecting members 30 are fixedly secured, in turn, to the vest 24 at mounting locations 33. This mounting arrangement provides a solid support for the rods 26 such that the vest 24 supports the entire cervical traction device 20.

Referring now to FIGS. 2-5, the expansion member 28 comprises a clamp 32 which slides over the support rod 26 and is secured in place by a clamp screw 34. A shaft 36 of the screw 34 threadably passes through an aperture 35 and engages the support rod 26 to fix the position of the clamp 32. The clamp 32 provides a base for the expansion member 28 relative to which adjustments may be made.

Figure 4:
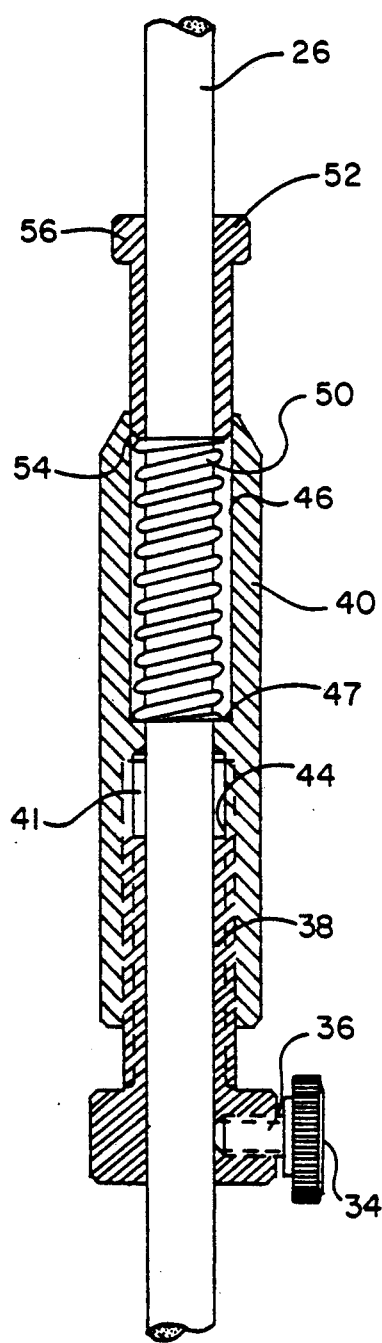
FIG. 4 is a sectional front elevational view of the support rod and adjustment means of FIG. 3.
Figure 5:
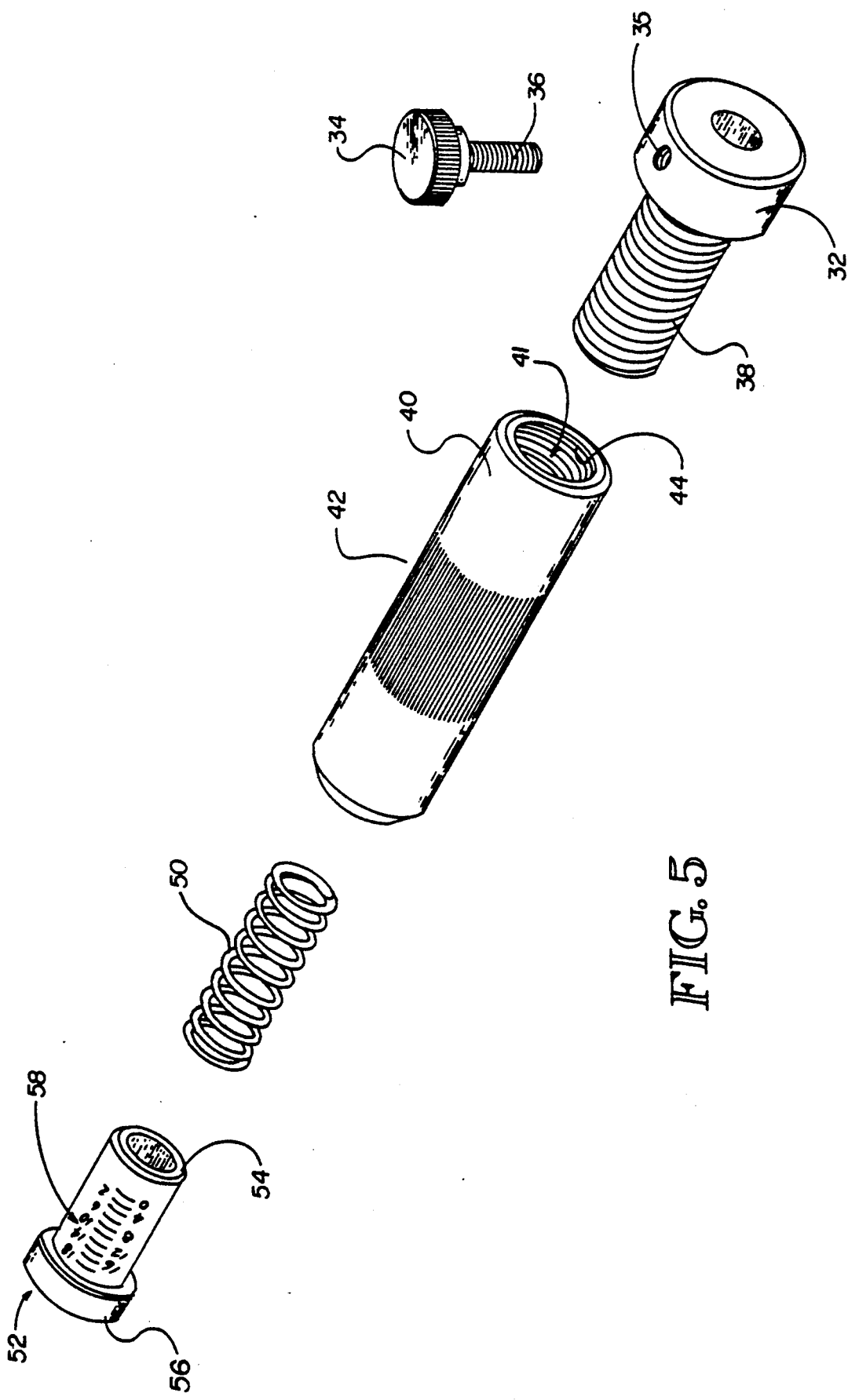
FIG. 5 is an exploded isometric view of the support means of the present invention.

With reference to FIGS. 4 and 5, an adjustment sleeve 40 has a threaded cavity 41 which is inserted over a threaded extension 38 of the clamp 32. The sleeve 40 also includes a knurled surface 42 which provides a surface suitable for grasping so the sleeve can be rotated to adjust the upward force exerted by the expansion member 28, the details of which are described below.

Referring to FIG. 4, the sleeve 40 further includes a cavity 46 having a seat 47. A biasing means or coil spring 50 is inserted over the support rod 26 immediately after the sleeve 40. The spring 50 engages seat 47, which provides a counteracting force when the spring 50 is compressed. In the disclosed embodiment, the spring 50 provides the primary upward force exerted on the halo 22.

A support insert 52 is inserted over the support rod 26 immediately following the coil spring 50. The insert 52 includes a bottom surface 54 which engages the spring 50 and an annular shoulder 56 which applies an upward force on the halo 22. The insert 52 is free to rotate about the support rod 26 and is held in place only by the forces the spring 50 and the coupling member 60 (discussed below).

the insert 50 additionally comprises printed indicia in the form of a calibrated scale 58 on one side which indicates the magnitude of force being applied to the halo 22. The scale 58 allows a precise, calibrated force to be applied to the halo 22 at each individual support rod 26. The indicia on the scale 58 may comprise any suitable standard of measure. The scale is easily readable after the traction device has been installed on the patient and allows for quick, accurate adjustments an time during use of the traction device.

Referring again to FIG. 1, a halo 22 is fixedly secured to a patient's head by a plurality of skull pins 23 passing through the halo at several locations about the patient's skull. Once the skull pins 23 have been secured in place, the halo 22 should not move relative to the patient's head. Although the embodiment shown in FIG. 1 shows a halo-type mounting arrangement for the skull, the present invention is suitable for other types of skull mounting arrangements.

A plurality of coupling members 60 are each secured at one end to the halo 22 by a bolt 62 and at another end to a support rod 26 by a pinch bolt 64. Each coupling member 60 can be adjusted three-dimensionally to secure the halo 22 to the support rods 26 in a proper position.

Figure 3:
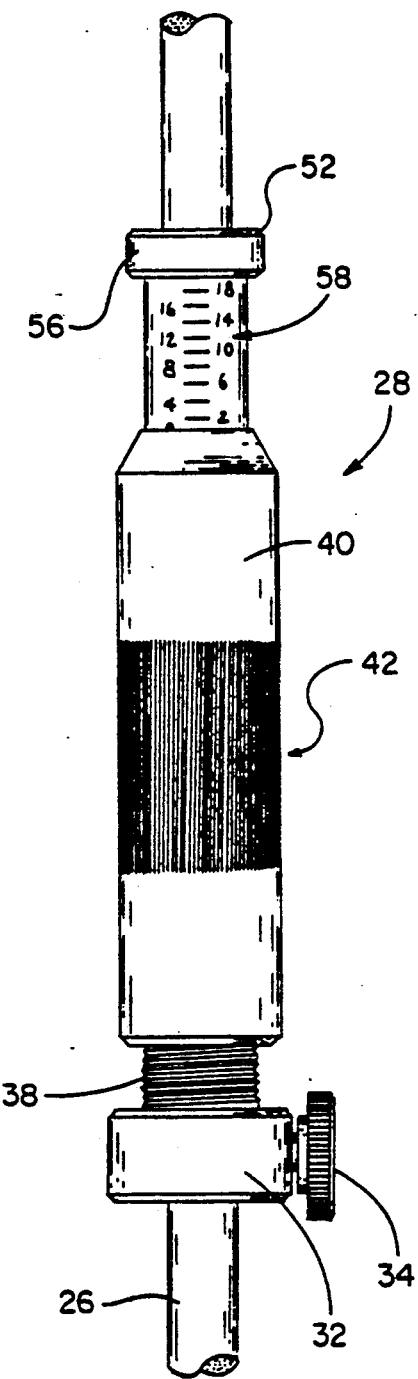
FIG. 3 is a partial side elevational view of a support rod and the adjustment means of the invention.

When an upward, supporting force of increased magnitude is desired, the pinch bolts 64 are loosened and the sleeve 40 is rotated in a counterclockwise direction (when viewed from above) relative to the clamp 32. This causes seat 47 to move upwardly and increase a compressive force being exerted by the spring 50 on the halo 22. As shown in FIG. 3, such an adjustment would reveal less of the scale, which would indicate an increase in the force being applied to the halo. Conversely, to decrease the magnitude of force, the sleeve is rotated in a clockwise direction to reduce the compressive force of the spring 50.

In operation, the halo 22 is first secured about the patient's skull by means of the skull pins 23. The vest 24 is then placed about the patient's torso and secured in place by means of the belt/buckle arrangements 29. The support rods 26 are subsequently attached to the vest 24 through connecting members 30. An expansion member 28 (i.e., the combined clamp 32, sleeve 40, spring 50, and support insert 52) is next inserted over each support rod 26. The coupling member 60 is then rigidly attached to the halo 22, although the pinch bolts 64 remain loose so that the coupling member 60 is free to slide on the support rods 26. The entire expansion member 28 is then moved so as to about the coupling member 60. With substantially no force being exerted on the halo 22 by the expansion member 28 at this point, the scale 58 can be adjusted and calibrated to correspond to the indicia indicating a zero magnitude of upward force. The clamps screws 34 are then tightened to secure the clamps 32 to their respective support rods 26. The sleeve 40 of each expansion member 28 is then rotated relative to the clamp 32 to adjust precisely the upward force exerted on the halo 22. The magnitude of the force will be displayed on the scale 58. After the upward force has been adjusted to the desired, predetermined magnitude for each support rod, each corresponding pinch bolt 64 is retightened to create a unitary cervical traction device.

From the foregoing, it will be appreciated that, although specific embodiments of the invention have been described herein for purposes of illustration, various modifications may be made without deviating from the spirit and scope of the invention. For example, the support rods 26 could remain slidably connected to the connecting members 30 while the expansion members 28 are adjusted to apply forces to the connecting members 30. Accordingly, the invention is not to be limited except as by the appended claims.

I claim:

1. A cervical traction device for supporting a patient's head during treatment of a neck or spinal injury, comprising:

a body support structure adapted to be worn about a patient's body;

a plurality of support rods coupled to and extending upwardly of the body support structure;

a halo adapted to be secured to the patient's head;

means for securing the halo to the support rods opposite the vest such that the support rods exert a supporting force on the halo; and adjustment means disposed between the halo and the body support structure for precisely adjusting the supporting force exerted by the support rods on the halo, the adjustment means including a means for measuring and displaying the magnitude of the supporting force.

2. A cervical traction device according to claim 1 wherein each support rod includes a means for measuring and displaying the magnitude of the supporting force such that a balanced, evenly distributed force can be applied to the halo.

3. A cervical traction device according to claim 2 wherein the measuring and displaying means comprises a calibrated scale for quantitatively displaying the force being applied to the halo.

4. A cervical traction device according to claim 1 wherein the adjustment means comprises an expansion member that can be adjusted telescopically to vary the supporting force applied to the halo.

5. A cervical traction device according to claim 4 wherein the measuring and displaying means comprises a calibrated scale for quantitatively displaying the force being applied to the halo, the scale operating in conjunction with the expansion member to display the amount of force applied to the halo.

6. A cervical traction device according to claim 4 wherein the supporting force is an upward, supporting force which enables the patient's neck or spine to be maintained in tension to allow proper healing of a neck or spine injury.

7. A cervical traction device according to claim 4 wherein the expansion member comprises a clamp fixedly attached to the support rod, a sleeve threadably secured at a first end to the clamp, a support insert being moveably disposed inside a second end of the sleeve for engaging and supporting the halo, a bias means disposed between the insert and the sleeve for providing an upward force on the support insert such that rotation of the sleeve causes the insert to move relative to the clamp to vary the upward force generated by bias means and, in turn, the supporting force applied to the halo.

8. A cervical traction device according to claim 2 wherein the bias means comprises a coil spring.

9. A cervical traction device according to claim 2 wherein two supports rods provide the supporting force on the halo, each of the support rods being adjusted individually to balance the supporting force.

10. A cervical traction device according to claim 2 wherein four support rods provide the supporting force on the halo, each of the support rods being adjusted individually to balance the supporting force.

11. A cervical traction device according to claim 1 wherein the body support structure comprises a vest adapted to be worn about the patient's torso.

12. A cervical traction device for supporting the head of a patient with a neck or spinal injury, comprising:

a vest adapted to be worn about a patient's torso;
a halo adapted to be secured to the patient's head;
multiple support rods, each support rod having a top end and a bottom end, the bottom end being fixedly coupled to the vest;
a coupling member interconnecting the halo and the top end of the support rod;
an expansion member coupled to the support rod for providing a supporting force to the halo, the expansion member comprising a clamp fixedly attached to the support rod, a sleeve threadably secured at a first end to the clamp, a support insert being moveably disposed inside a second end of the sleeve, a bias means disposed in-between the insert and the sleeve for providing an upward force on the support insert such that rotation of the sleeve causes the insert to move relative to the clamp to vary the upward force generated by bias means and, in turn, the supporting force applied to the halo; and
each support rod including a calibrated scale for measuring and displaying the magnitude of the supporting force such that a balanced, evenly distributed force can be applied to the halo.

13. A cervical traction device according to claim 12 wherein the bias means comprises a coil spring.

14. A cervical traction device according to claim 12 wherein two support rods provide the supporting force on the halo, each of the support rods being adjusted individually to balance the supporting force.

15. A cervical traction device according to claim 12 wherein four support rods provide the supporting force on the halo, each of the support rods being adjusted individually to balance the supporting force.

16. A method for securing a cervical traction device in place on a patient with a neck or spinal injury, comprising the steps of:

placing a vest about a patient's torso;
securing a halo to the patient's head;
interconnecting the vest and the halo by means of multiple support rods, each support rod providing an upward supporting force to the halo;
individually adjusting the supporting force applied by the support rods to achieve a balanced supporting force applied to the halo; and
viewing a calibrated scale on each support rod to determine precisely the force being applied to the halo by each support rod.

* * * * *